United States Patent [19]
Pfefferle et al.

[11] Patent Number: 5,605,080
[45] Date of Patent: Feb. 25, 1997

[54] SCREW DRIVER

[75] Inventors: Joachim Pfefferle, Munstertal; Michael Roth, Ebringen; Peter Scheuble, Wasenweiler; Hermann Zeuner, Freiburg, all of Germany

[73] Assignee: Elekta Instrument GmbH, Umkirch, Germany

[21] Appl. No.: 562,967

[22] Filed: Nov. 27, 1995

[30]     Foreign Application Priority Data

Nov. 25, 1994 [DE] Germany .......................... 44 41 965.1

[51] Int. Cl.⁶ ..................................................... B25B 23/08
[52] U.S. Cl. .................................. 81/456; 81/438; 81/452
[58] Field of Search .............................. 81/438, 451–453, 81/456–458

[56]                References Cited

U.S. PATENT DOCUMENTS

| 885,280 | 5/1907 | Campbell . |
| 1,441,956 | 1/1923 | Watson . |

FOREIGN PATENT DOCUMENTS

| 3110776A1 | 12/1981 | Germany . |
| 8403371 U | 5/1984 | Germany . |
| 3539502C1 | 2/1987 | Germany . |
| 3804749C2 | 5/1991 | Germany . |
| 9310668 U | 12/1993 | Germany . |
| 369416 | 6/1963 | Switzerland . |

*Primary Examiner*—James G. Smith
*Attorney, Agent, or Firm*—Baker & Daniels

[57]                ABSTRACT

The present invention involves screwdriver having a grip, a driver blade insertable into and rotationally affixed to said grip and a chuck. The chuck encloses and is longitudinally displaceable relative to the driver blade. The chuck has collets extending from an end disposed near the blade tip. The collets have claws extending from their free ends which are adapted to retain a screw on the blade tip when the chuck is in a retaining position. The collets may be either inwardly biased or outwardly biased. A sleeve, for pressing the collets inward, is provided for embodiments employing outwardly biased collets. A stop device is provided for inhibiting the longitudinal displacement of the chuck towards the blade tip beyond the retaining position. The stop device comprises a groove in the blade shaft and a cooperating detent spring located on the chuck. The free end of the detent spring extends toward the blade tip and is biased inward so that it is disposed within the groove. When the chuck is in the retaining position the detent spring bears against a stop face of the groove thereby inhibiting further longitudinal displacement of the chuck relative to the blade.

30 Claims, 8 Drawing Sheets

SCREW DRIVER

BACKGROUND OF THE INVENTION

The present invention relates to screwdrivers, more specifically, to screwdrivers for bone screws.

A two part screwdriver with a grip part can be comprised of a driver blade and a chuck. The driver blade features a tip and is adapted for insertion into the grip part and is secured against rotation and unintentional removal relative to the grip part by means of a locking device. The chuck retains a screw which meshes with the blade tip, encloses the driver blade and allows displacement of the driver blade in the longitudinal direction. The displacement of the chuck is limited by a stop device when the chuck reaches a retaining position. The chuck possesses collets biased in the direction of the driver blade and has claws on the ends of the collets.

A three part screwdriver with a grip part can be comprised of a driver blade, a chuck and a sleeve. The driver blade features a tip and is adapted for insertion into the grip part and is secured against rotation and unintentional removal relative to the grip part by means of a locking device. The chuck retains a screw which meshes with the blade tip, encloses the driver blade and allows displacement of the driver blade in the longitudinal direction. The displacement of the chuck is limited by a stop device when the chuck reaches a retaining position. The chuck possesses collets biased away from the driver blade and has claws on the ends of the collets. A sleeve encloses the chuck, allows longitudinal displacement of the chuck and forces the outwardly biased collets toward the driver blade.

A screwdriver according to the initially cited two-part, inward biased, design is known from U.S. Pat. No. 1,441,956. Provided on this screwdriver is, cross-sectionally, an essentially quadratic driver blade, with a tip, which is surrounded by a longitudinally slidable chuck. For retaining a screw, the chuck possesses collets which are biased inwardly toward the driver blade, with claws on their ends. Provided as stop device for limiting the displacement of the chuck are four paired and opposed roundish grooves recessed in corresponding side surfaces of the chuck as well as two opposed projections pointing in the direction of the driver blade. Furthermore, the chuck is provided with a slot-shaped recess which is engaged by a pin arranged on the driver blade. The length of the recess matches the spacing of the groove pairs. The arrangement of the recess and the pin is such that, as the projections engage mutually opposed groove pairs, the pin strikes one end of the recess.

For grabbing a screw, the chuck is disposed in its front limiting position, in which the projections engage the grooves in the driver blade near the blade tip. A screw is insertable between the claws protruding beyond the blade tip when the collets are forced open. The screw is then retained by the inward bias of the collets. To mesh the screw with the blade tip, the chuck is retractable in the direction of the blade tip until the projections reach their retaining positions in the grooves pointing away from the blade tip. Thus, there are two defined positions of the chuck relative to the driver blade which allow easy adjustment.

The removal and restoration of the pin of this design make assembly and disassembly unsuitably expensive. This two-part screwdriver has the additional disadvantage that, as the chuck is being displaced between its retaining position and its front limit position, the projections run onto a section of the driver blade that has an enlarged cross section thereby reducing the retaining tension of the claws. As a result of the reduced tension, a screw can unintentionally drop-out relatively easily, for instance, when touching a side wall, under congested conditions. Moreover, once a screw has been placed, there is the risk of injuring sensitive biological tissue by bumping into it if the lateral forces necessary for chuck release are exerted under congested space conditions.

Known from DE 35 39 502 C1 is a screwdriver according to the initially cited three-part, outwardly biased, design. In this prior three-part screwdriver there is a driver blade surrounded by a longitudinally displaceable chuck which, in its end area near the tip, features outwardly biased collets with claws for retaining a screw. The collets are outwardly biased due to the relatively high outward spring tension of the collets. The chuck is surrounded by a longitudinally slidable retaining sleeve. By sliding the retaining sleeve toward the blade tip, the outwardly biased claws are longitudinally entrained by the chuck beyond the tip of the driver blade and are pressed inward to engage the screw head by the relative movement of the retaining sleeve over the collets. The movement of the retaining sleeve is a relatively energy-intensive action. To prevent the claws from sliding beyond the screw head, the driver blade is equipped with an annular shoulder of increased circumference which strikes a stop shoulder of the chuck at the level of the screw head when the claws reach a retaining position thereby preventing further advancement of the chuck.

To preclude an unintended displacement of the chuck in response to gravitational forces on the driver blade, for one, and of the retaining sleeve on the chuck for another, recesses and/or longitudinal slots with sections biased in the direction of the driver blade need to be provided in the chuck and retaining sleeve areas near the grip part. The recesses and/or slots are provided so that, due to the elevated frictional forces created by the sections bearing under bias, a displacement will take place only when intentionally actuated by the user. The defined adjustment of the friction forces makes fabrication relatively expensive. Additionally, necessary corrections, for example, due to damage in the screwdriver assembly attributable to the complex interaction of the various forces, are only possible with difficulty. Furthermore, due to the high outward bias of the collets, the user must exert relatively great forces to assemble the screw driver, and, during disassembly for cleaning, the risk of injury is undesirably high due to the numerous sharp edges.

In order for the chuck to be reliably advanced to its retaining position as the retaining sleeve is displaced toward the blade tip, the collets must expand relatively far outward, even when highly biased. This creates disadvantages not only during the assembly of the screw driver but also when the assembly is used in congested spaces and can result in injuries to biological tissues.

Known from CH-PS 369,416 is another three-part, outwardly biased, screwdriver that features a chuck surrounding a driver blade and having collets that are fitted on their ends with outwardly bent open claws. The collets are surrounded by a retaining sleeve for forcing the claws towards the driver blade in the area of a blade tip. The retaining sleeve possesses an inhibitory spring which is bent inward in the direction of the chuck and serves to enhance the frictional resistance between the chuck and the retaining sleeve. In this latter three-part screwdriver, the chuck and the retaining sleeve are independently displaceable by means of dish grips, however, defined positions to facilitate reliable operation are not provided. Instead, the user must take care that the chuck is correctly positioned relative to the driver blade and that advancing the retaining sleeve does not allow a retained screw to come off the driver blade. This is an extremely cumbersome process and is nearly impossible where the visibility of the screwing site is poor or nonexistent.

Known from DE 31 10 776 A1 and U.S. Pat. No. 855,280 are screwdrivers featuring driver blades surrounded by a chuck with a slip-over retaining sleeve. Such screwdrivers, while provided with defined positions, are nonetheless costly to assemble and disassemble. In the case of DE 31 10 776 A1, defined positions are achieved with expensive toggle lever mechanisms arranged on the retaining sleeves which require spring-supported toggle levers to engage recesses in the chucks.

Known from DE 84 03 371 U1 is a telescoping support where an interior tube is movable relative to an exterior tube by means of a tapped ring which is rotatable on an external threading of the internal tube and bears on one end of the external tube. To prevent the internal tube from slipping out of the external tube, a tongue type locking member in the form of a leaf spring, arranged on the external tube, is biased in the direction of the internal tube and engages in its limit position a groove recessed in the internal tube, thereby blocking a further displacement of the internal tube relative to the external tube.

SUMMARY OF THE INVENTION

The objective underlying the invention is to create screwdrivers of the abovementioned types which are simple to manufacture, easy to disassemble and re-assemble for cleaning purposes, are adjustable to defined manipulating positions with little force, and can be used reliably under congested space conditions at sites with poor visibility or none at all.

This objective is accomplished with the two-part screwdriver with a stop device featuring a groove recessed in the driver blade and a chuck fitted with at least one tongue type leaf spring pointing in the direction of the blade tip and biased in the direction of the driver blade as a stop device. The free end of the leaf spring fits in the groove and bears on the end face of the groove nearest the blade tip when the chuck is in the retaining position. The driver blade features a bevel in the tip area upon which the claws bear when in a retracted release position. The claws can be slipped onto the blade shank only by exerting additional force.

This objective is accomplished with the three-part screwdriver with a stop device featuring a groove recessed in the driver blade and a chuck fitted with at least one tongue type leaf spring pointing in the direction of the blade tip and biased in the direction of the driver blade. The free end of the leaf spring fits into the groove and bears upon the groove end face nearest the blade tip when the chuck is in the retaining position. The sleeve features an inhibitory spring biased in the direction of the chuck and having the shape of a leaf spring to enhance the friction force present during longitudinal displacement between the chuck and the sleeve. The material thickness of the collets is greatest nearest the claws. The driver blade has a bevel in its tip area so that the heavier sections of the collets bear between the bevel and the blade tip when the chuck is in the retaining position and the sleeve is slipped on the claws.

Thus, a front stop is provided by a groove recessed in the driver blade and a leaf spring on the chuck which fits in the groove and thereby prevents the chuck from unintentionally being slipped beyond the head of a screw. The leaf spring bias is easily adjustable by bending the leaf spring in the appropriate amount and direction, so that the user may readily and reliably make a correction of the friction force. Neither the recessed groove in the driver blade nor the fashioning of a leaf spring on the chuck creates a problem during fabrication, use, or cleaning of the screwdriver. Assembly and disassembly are easy to perform, with little expense of force and little risk of injury. Assembly is accomplished by nesting the driver blade and the chuck until the free end of the leaf spring snaps into the groove. Damage to the leaf spring, with a resultant unfavorable change of bias, is thereby greatly reduced.

Furthermore, by providing the two-part embodiment with a bevel in the tip area, a further stop is created which prevents an unintended excessive retraction of the chuck. The cross-sectional reduction in the tip area also makes for a particularly small blade tip enabling safe working under congested space conditions with limited visibility.

With the three-part embodiment, providing an inhibitory spring biased toward the chuck allows, on account of the enhanced frictional resistance, the use of collets having a small outward bias. Thus, the claws protrude only little away from the blade tip and assembly of the screwdriver is eased due to the relatively small forces required to compress the collets. Furthermore, providing the bevel in the tip area results in a slender overall cross-section of the screwdriver thereby facilitating use in congested spaces and in poor visibility.

BRIEF DESCRIPTION OF THE DRAWINGS

The above mentioned and other features and objects of this invention, and the manner of attaining them, will become more apparent and the invention itself will be better understood by reference to the following description of exemplary embodiments of the invention taken in conjunction with the accompanying drawings, wherein.

DESCRIPTION OF THE PRESENT INVENTION

The embodiments disclosed below are not intended to be exhaustive or limit the invention to the precise forms disclosed in the following detailed description. Rather, the embodiments are chosen and described so that others skilled in the art may utilize their teachings.

Figure 1:
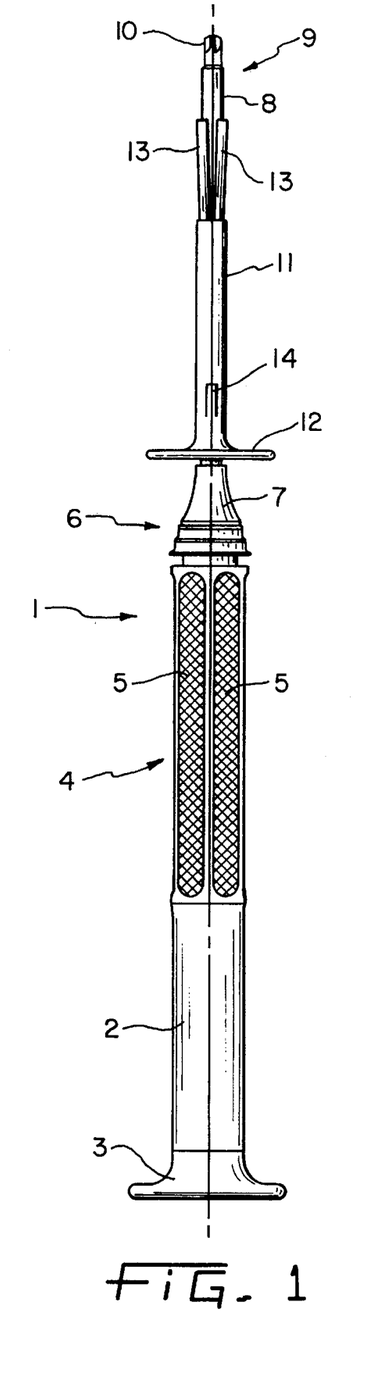
FIG. 1 is a view of an embodiment of a screwdriver according to the invention featuring a displaceable chuck on a driver blade.

FIG. 1 shows an embodiment of a screwdriver 1 according to the invention, with a grip part 2, at the head of which a dish support 3 rotatable relative to the grip part 2 is arranged. The grip part 2 features in the gripping area 4 several gripping fields 5 provided with a knurling that guarantees a nonslip turning of the grip part 2.

Provided on the grip part 2 end opposite the dish support 3 is a locking device 6, in the mouthpiece 7 of which a driver blade 8 can be inserted. The driver blade 8 possesses in its tip area 9 a tip 10 of a design complementary to that of the screw to be placed. The exemplary embodiment of FIG. 1 illustrates a driver blade 8 with a tip 10 adapted for screwing surgical bone screws in place.

The driver blade 8 is enclosed by a chuck 11 displaceable in the longitudinal direction of the driver blade 8. The chuck 11 features on its end near the grip part a displacement dish 12 with the aid of which a user of the screwdriver 1 is able to move the chuck 11 easily on the driver blade 8. In its tip area 9, the chuck 11 is fitted with collets 13 which are biased toward the driver blade 8 and bear on it with a contact pressure determined by the inward bias and the diameter of the driver blade 8. In the exemplary embodiment shown in FIG. 1, a detent spring 14 in the form of a leaf spring is provided which is biased toward the driver blade 8 and made integrally with the chuck 11.

Figure 2:
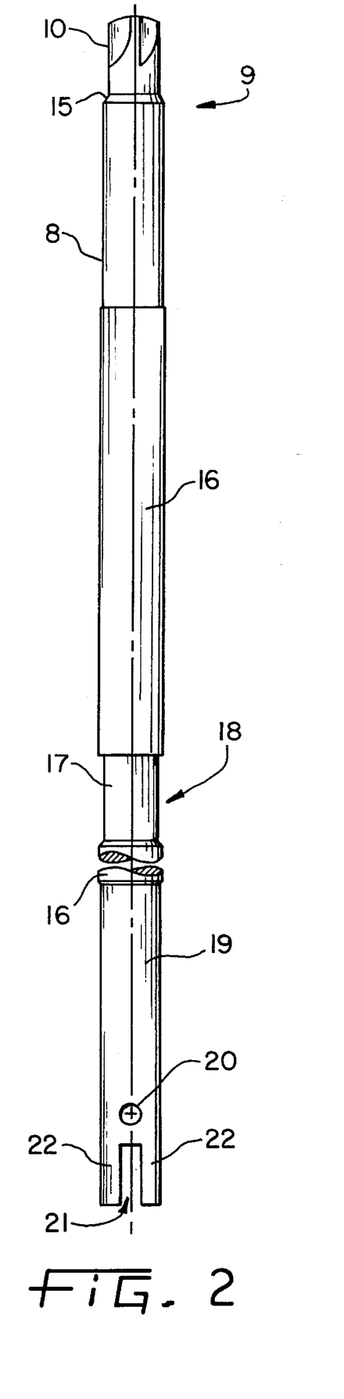
FIG. 2 is a view of a driver blade with a peripheral groove.

FIG. 2, shows, as a truncated illustration, an embodiment of the driver blade 8. The blade tip 10 extends in the tip area 9 via a bevel 15 into a blade shank 16 into which, in the peripheral direction of the driver blade, a locking groove 18 is recessed, on a detent section 17. Provided on the end of the driver blade 8 opposite the blade tip 10 is a locking section 19 that features a locking bore 20 and two locking tongues 22 forming a yoke with an insertion slot 21.

Figure 3:
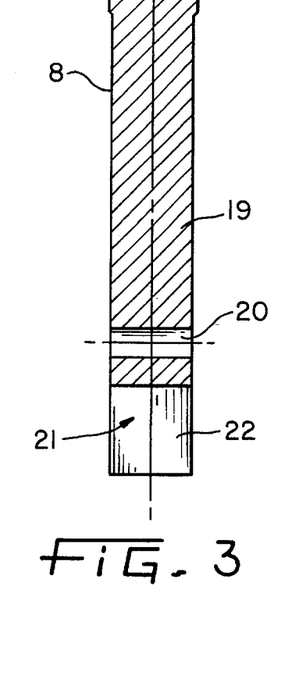
FIG. 3 is a cross sectional view of the embodiment of the driver blade according to FIG. 2 near the grip part.

FIG. 3 shows in a sectional view the locking bore 20 traversing the locking section 19, as well as one of the locking tongues 22.

Figure 4:
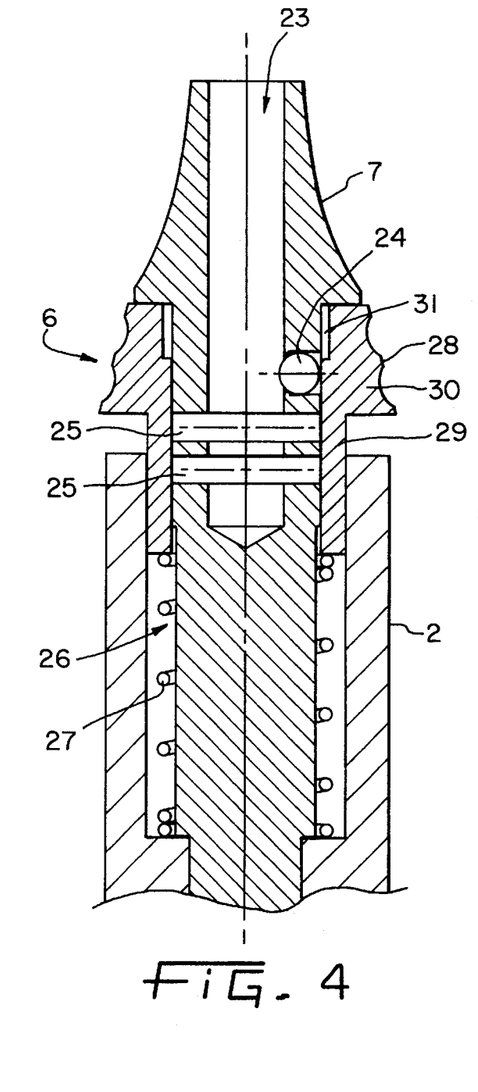
FIG. 4 is a cross sectional view of a locking device for receiving a driver blade according to FIG. 2.

FIG. 4 shows in a sectional view a preferred embodiment of a locking device 6. Its mouthpiece 7 is joined firmly to the grip part 2 and features a blade mount 23 into which fits the locking section 19 of the driver blade 8. Movable transverse to the longitudinal axis of the blade mount 23, a locking ball 24 is fitted in a wall recess, on the end of the blade mount 23 near the grip part. Between the locking ball 24 and the end of the blade mount 23 near the grip part there are two safety pins 25 provided for insertion in bores, sideways in the mouthpiece 7, prior to insertion in the grip part 2. The mouthpiece 7 screws in this exemplary embodiment with its threaded section into a tapped section of the grip part 2.

The grip part 2 possesses on its end near the mouthpiece a recess whose cross-sectional area is larger than the section of the mouthpiece 7 protruding into the grip part 2. Provided in a cavity 26 thus created between the grip part 2 and the mouthpiece 7 is a compression spring 27 which, for one, bears on the bottom surface of the cavity 26 and, for another, on an annular surface, of a locking ring 28, protruding into the cavity 26. The locking ring 28 bears with its outside wall on the wall of the cavity 26 and with its inside wall on the outside surface of the mouthpiece 7. The locking ring 28 features a hollow cylinder section 29 inserted in the cavity 26 and an actuating section 30 which, peripherally enlarged, protrudes beyond the grip part 2. The hollow cylinder section 29 is adapted for insertion in the cavity 26, with the compression spring 27 bearing on its inside annular surface.

On the end of the actuating section 30 away from the grip part 2 there is a recessed annular groove 31 which enlarges the inner circumference of the actuating section 30 and allows the locking ball 24, with the locking ring 28 retracted against the force of the compression spring 27, to enter annular groove 31 a sufficient distance such that the surface area of the locking ball 24 bordering on the blade mount 23 is flush with the wall of the blade mount 23, leaving the full cross section of the blade mount 23 open for insertion of the locking section 19 of the driver blade 8. The mouthpiece 7 bulges peripherally where it engages the locking ring 28, creating for the locking ring 28 a stop, acting against the force of the compression spring 27.

Figure 5:
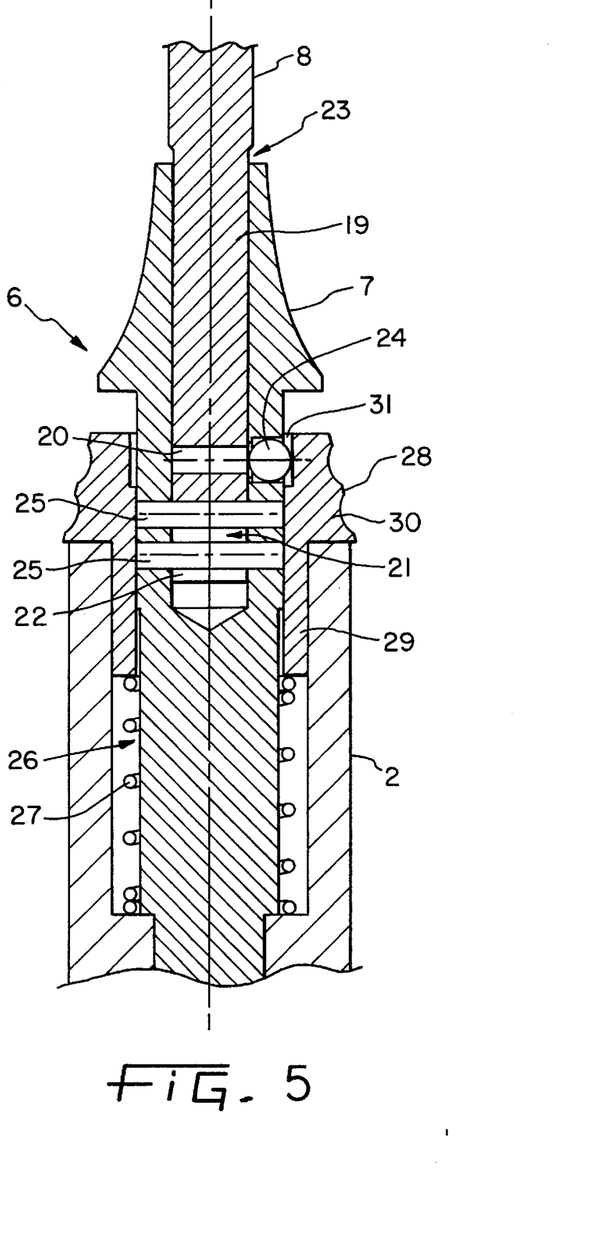
FIG. 5 is a cross sectional view of the locking device according to FIG. 4, with a driver blade inserted in nonfixed position.

FIG. 5 shows the locking device 6 according to FIG. 4 with the locking section 19 of the driver blade 8 according to FIG. 2 inserted in the blade mount 23. The locking ring 28 is illustrated in a position retracted against the force of the compression spring 27 and bearing on the grip part 2. The locking ball 24 is in a displaced position so as to engage the annular groove 31 in the actuating section 30 of the locking ring 28 and is arranged in extension of the locking bore 20 of the driver blade 8. The safety pins 25 traverse the insertion slot 21 formed by the locking tongues 22, with the closed end of the insertion slot 21 engaging the first safety pin 25.

Figure 6:
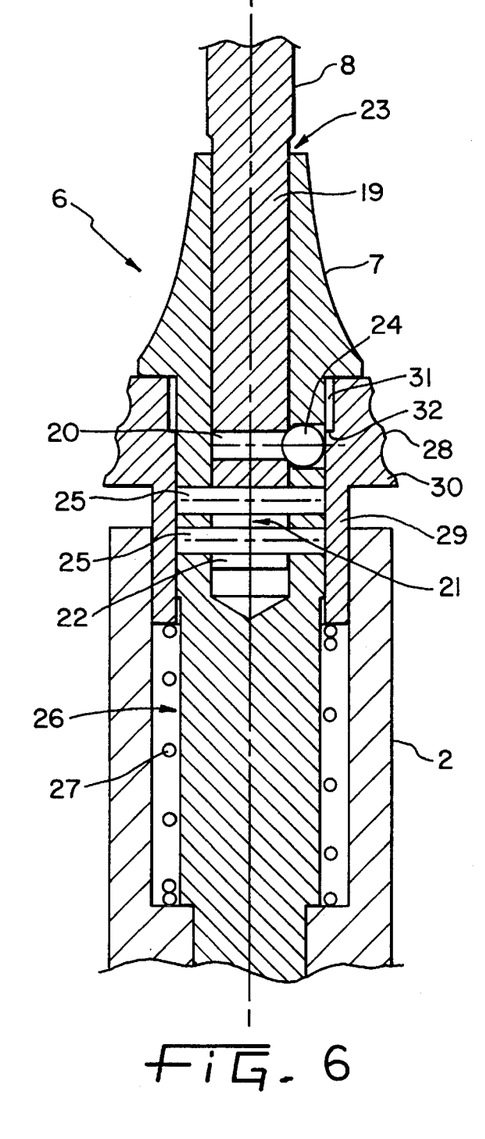
FIG. 6 is a cross sectional view of a locking device according to FIG. 5 in a position fixing the driver blade.

FIG. 6 shows the locking device 6 according to FIG. 5 with the driver blade 8 inserted and locked. The compression spring 27 is in a maximally relieved position and pushes the actuating section 30 of the locking ring 28 against the stop formed by the peripherally enlarged section of the mouthpiece 7. As the locking ring 28 moves from the release position, illustrated in FIG. 5, to the locking position, illustrated in FIG. 6, the locking ball 24 is shifted, as it passes the stepped end face 32 of the annular groove 31, and it engages the locking bore 20. The driver blade 8 is thus secured against pull-out by the fixed locking ball 24 and against rotation relative to the grip part 2 by the safety pins 25 traversing the insertion slot 21.

The locking device illustrated in FIG. 4 through 6 is characterized by a high rotational load capacity. The safety pins 25 traversing the yoke type insertion slot 21 guarantee with close-fit fabrication a durable seating which does not experience backlash even in applications involving high torques.

Figure 7:
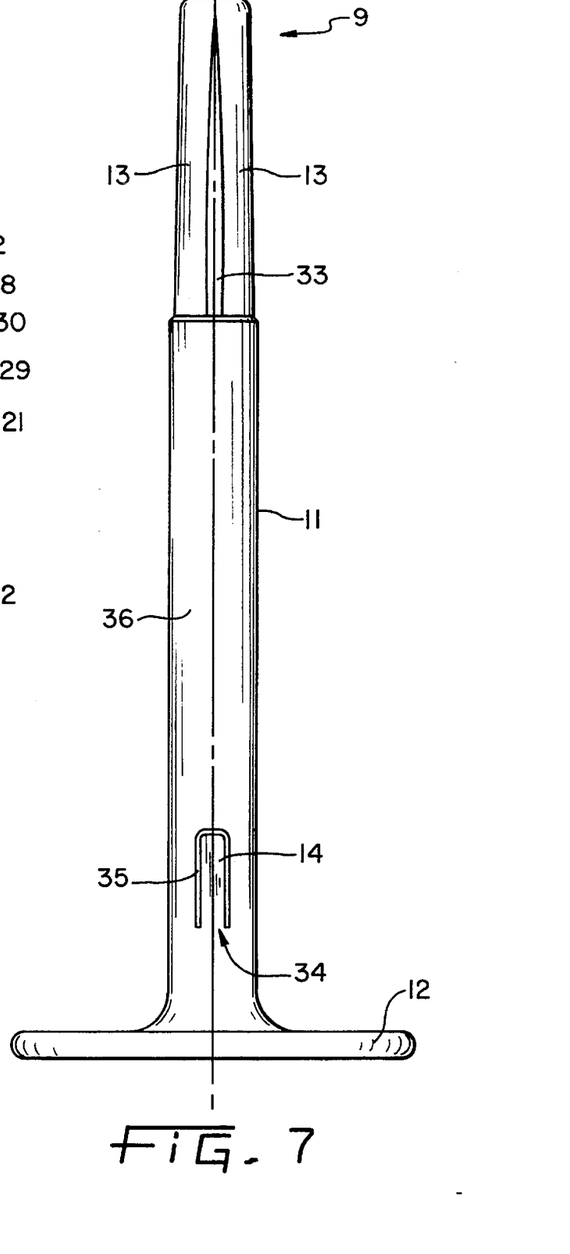
FIG. 7 is a view of a chuck fitted with a leaf spring and inwardly biased collets.

FIG. 7 shows the chuck 11, at a larger scale than FIG. 1, with the driver blade 8 removed. The collets 13, due to their inward bias, bear on one another in the tip area 9, forming a converging collet slot 33. In the embodiment illustrated in FIG. 7, the tongue type detent spring 14 is of rectangular design and fabricated integrally with the chuck 11. The detent spring 14 may be formed by cutting—starting on one bottom side 34—a curvilinear contour slot 35 in the shank 36 of the chuck 11, using, for example, a laser beam.

Figure 8:
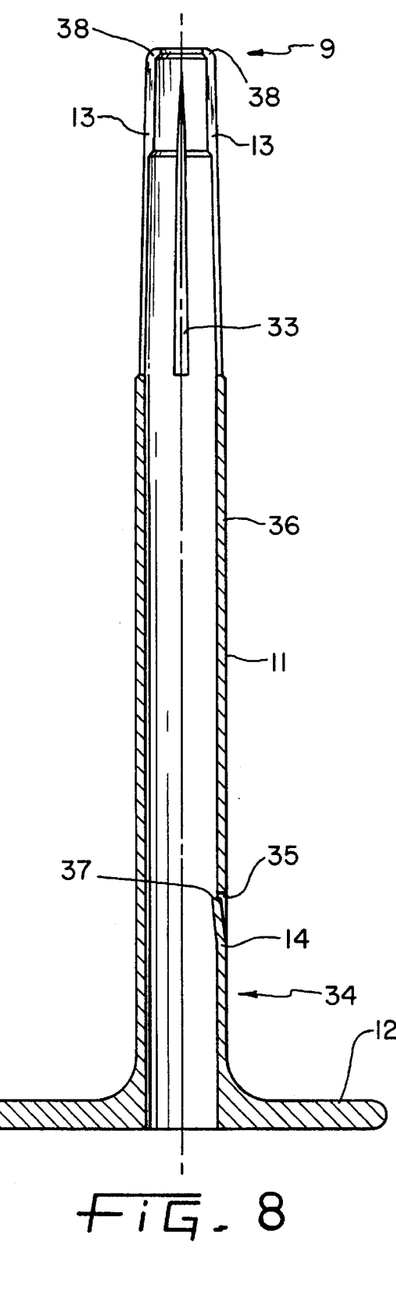
FIG. 8 is a cross sectional view of the chuck according to FIG. 7.

FIG. 8 shows in a sectional view the chuck 11 according to FIG. 7 with the detent spring 14 biased inward. The detent spring 14 is bent inward at least one-half the material thickness of the chuck shank 36, forming with its free end a stop face 37 which protrudes into the interior cavity of the chuck 11. Additionally, it is evident from FIG. 8 that the inwardly biased collets 13 have, on their ends, claws 38 which are bent toward the center axis of the chuck 11 and adapted for gripping the head of a screw.

Figure 9:
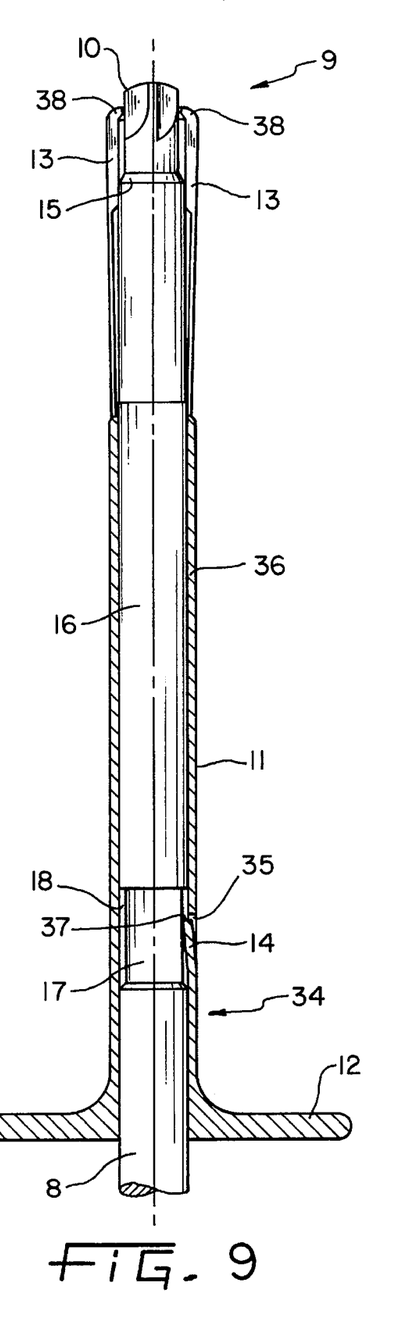
FIG. 9 is partially cross sectional view of the blade according to FIG. 2 fitted in the chuck according to FIG. 7.

FIG. 9 shows, in a partly sectional view, the driver blade 8 according to FIG. 2 with the chuck 11 shown in FIG. 8 slipped over the blade tip 10. The claws 38 bear with a contact pressure in the tip area 9 on the driver blade 8, with the collets 13 forced open and generating friction forces in displacement. The detent spring 14 engages the locking groove 18 and bears with a bias that generates friction forces on the locking section 17 of the driver blade 8. Said friction forces are easily adjustable by bending the detent spring 14 and the collets 13 in the appropriate amount and direction. In a displacement of the chuck 11 away from the blade tip 10, the bevel 15 on the blade forms a rear stop for the claws 38, so that slipping the jaws 38 onto the blade shaft 16 is possible only in conjunction with an intended displacement of the chuck 11 requiring an increased exertion of force.

Figure 10:
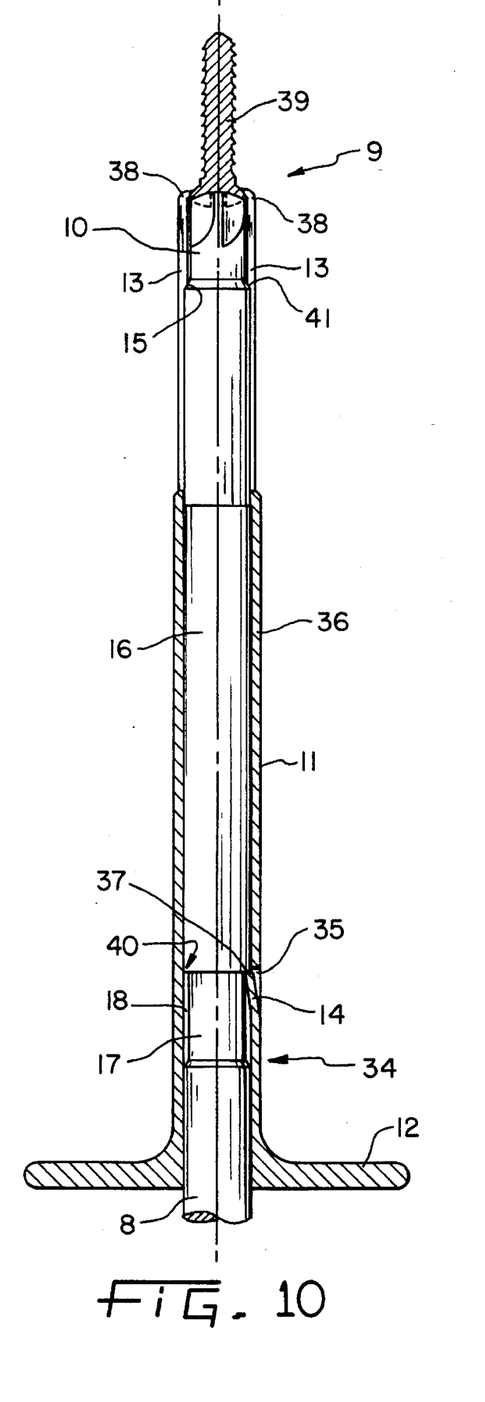
FIG. 10 is a partially cross sectional view of the arrangement according to FIG. 9 with the chuck retaining a screw meshing with the blade.

FIG. 10 shows the chuck 11 and driver blade 8, according to FIG. 9, in the retaining position, with a bone screw 39 meshing with the blade tip 10. The stop face 37 of the detent spring 14 engages the limit face 40 of the locking groove 18 nearest the blade tip when the assembly is in the retaining position. The claws 38 grip the head of the bone screw 39 due to the inward bias of the collets 13. The contact pressure between collets 13 and bone screw 39 retains the bone screw 39 reliably, allowing, for instance, its transport from a screw container to the screw-in site.

The chuck 11 is retractable for release of the bone screw 39. As can be seen from FIGS. 8 through 10, the slip-off of the claws 38 from the head of the screw 39 is aided by a simultaneous engagement of a beveled step 41 with the expansion bevel 15 of the driver blade 8. The angle of the blade bevel 15 preferably matches the bevel on the bottom side of the head of screw 39, thereby avoiding an undesirable exertion of axial forces on the screw 39. When the chuck 11 is in the retaining position and the bone screw is being turned, contact between the claws 38 and the substrate results in a forced opening of the claws 38.

Fitting a screwdriver 1 with a chuck 11 where the collets 13 are biased inwardly in the direction of the driver blade 8 has, from the viewpoint of handling, the advantage that only two components need to be nested, namely the driver blade 8 and the chuck 11. The chuck 11 being slipped over the blade tip 10 after the introduction and locking of the driver blade 8 into the grip part 2. Moreover, use of the screwdriver 1 in bone surgery reduces cleaning requirements since only two parts make direct contact with the tissue and need to the cleaned.

Figure 11:
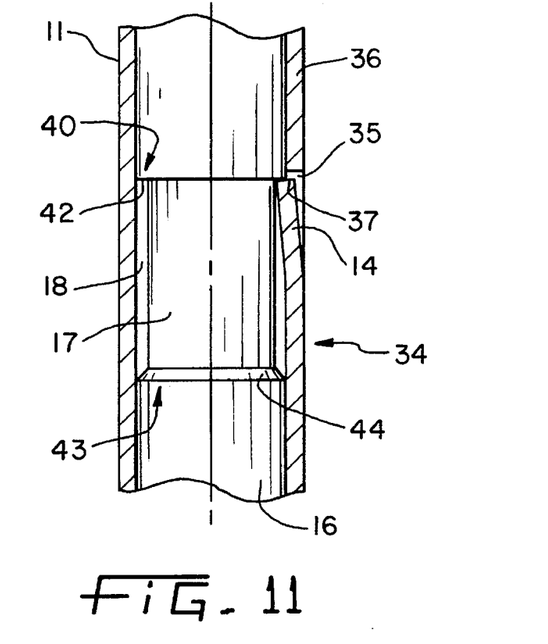
FIGS. 11 through 13 are partial cross sectional views of various embodiments of the grooves and leaf springs with the chuck in the retaining position.
Figure 12:
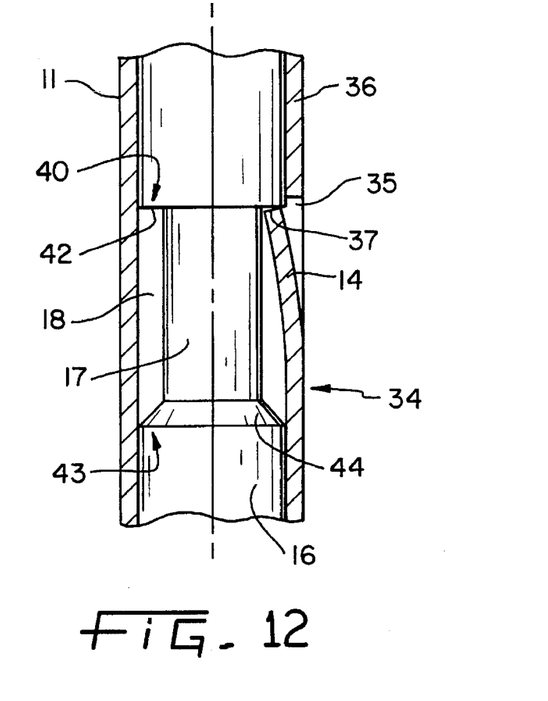
Figure 13:
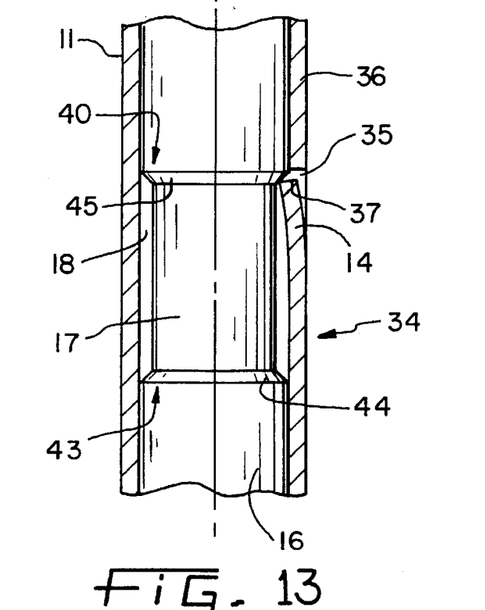
Figure 14:
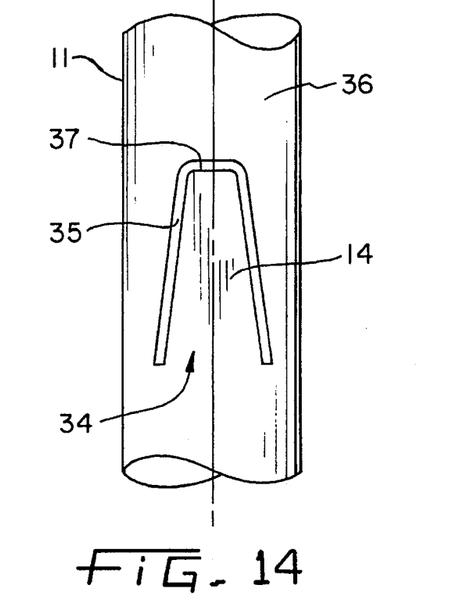
FIGS. 14 through 17 are views of various embodiments of leaf springs.

Illustrated in FIGS. 11 through 13 are various embodiments of the locking groove 18 and detent spring 14. In FIG. 11, the limit face 40 of the locking groove 18, nearest the blade tip, on the locking section 17 of the blade shank 16, is machined in the peripheral direction to a depth corresponding to about one-half the material thickness of the chuck shank 36. This provides a stop face 42 which is rectangular relative to the longitudinal direction of the driver blade 8. The detent spring 14 is biased sufficiently inward for the stop face 37 to bear across the entire height of the stop 42 on the limit face 40 nearest the blade tip. The limit face 43 nearest the grip end, opposite the stop face 40 nearest the blade tip, is fashioned as a spring run-on bevel 44 onto which the detent spring 14 slips as the driver blade 8 is displaced.

In the embodiment according to FIG. 12, the locking groove 18 is recessed to a depth greater than the material thickness of the chuck shaft 36. The detent spring 14 is, in the embodiment shown in FIG. 12, biased sufficiently inward for its stop face 37 to bear completely on the stop 42, precluding an overshooting of the limit face 40 by the stop face 37 of the detent spring 14, even with the exertion of great force and a worn stop 42.

The embodiment shown in FIG. 13 has a locking groove 18 depth similar to the embodiment shown in FIG. 11 but with the limit face 40 nearest the blade tip fashioned as a beveled stop 45. This impedes, for one, an unintended overshooting of the limit face 40 by the stop face 37 of the detent spring 14, due to the inward bias of detent spring 14. On the other hand, however, appropriate exertion of force makes it possible to remove the chuck 11 from the driver blade 8 by slipping the chuck forward in the direction of the blade tip 10 without requiring a release of the connection between the grip part 2 and the driver blade 8. To obtain high slip-over forces the beveled stop 45 is given a large angle of inclination, whereas a small angle of inclination can be used to obtain relatively low slip-over forces.

Figure 15:
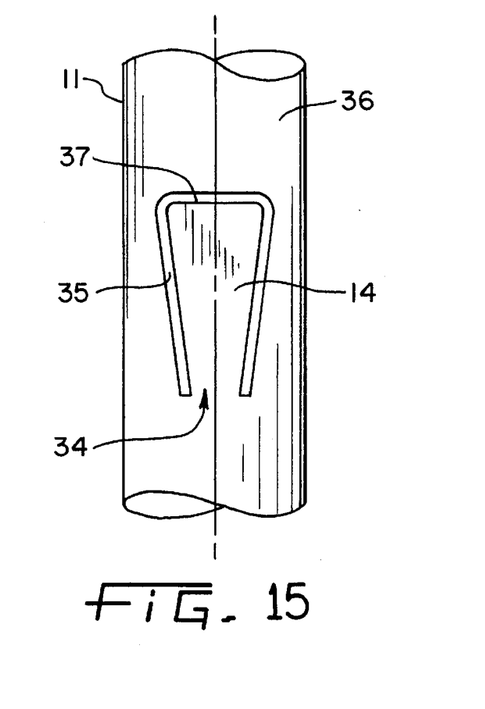

FIGS. 14 through 17 show various embodiments of detent springs 14. In the embodiments according to FIGS. 14 and 15, the detent springs 14 are fashioned as a trapezoid with identical side lines. The detent shown in FIG. 14 has a bottom side 34 being formed by the longer baseline and the stop face 37 by the shorter baseline of the trapezoid. In the embodiment according to FIG. 15, on the other hand, the bottom side 34 is formed by the shorter baseline, and the stop face 37 by the longer baseline of the trapezoid. The embodiment shown in FIG. 14 allows relatively little alteration in use once the bias has been adjusted compared to the embodiment shown in FIG. 15. The embodiment according to FIG. 15 is characterized by a relatively long stop face 37 which effectively prevents an unintended overshooting of the limit face 40.

Figure 16:
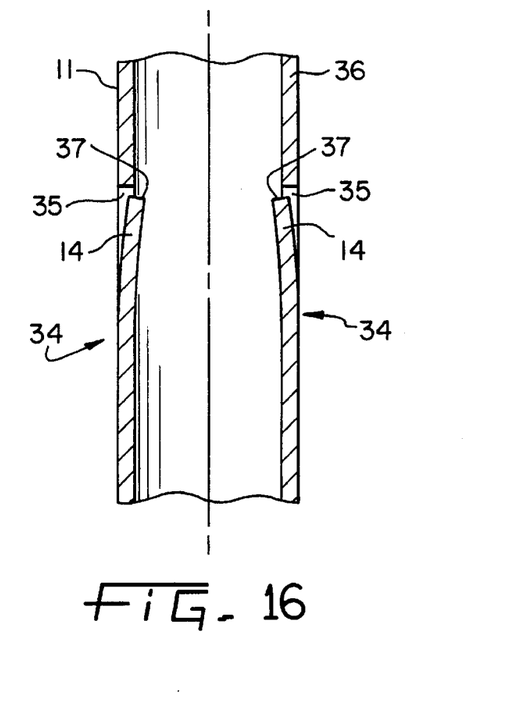
Figure 17:
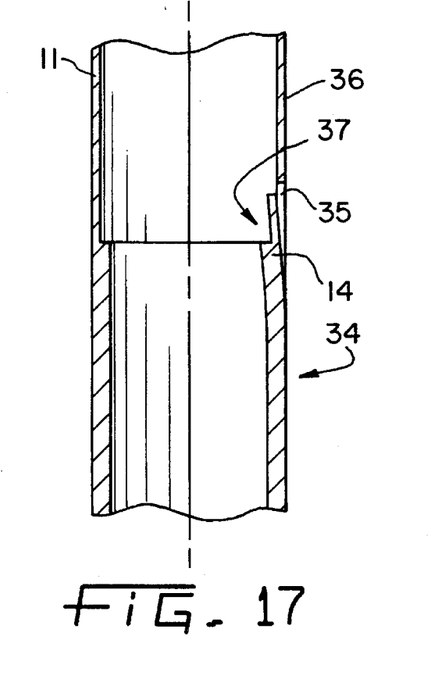

The embodiment shown in FIG. 16 features two detent springs 14 which are both inwardly biased and effectively prevent an overshooting of the limit face 40 by the stop faces 37, even with a worn detent spring 14. FIG. 17 shows the embodiment of a detent spring 14 with a stepped stop 37 that engages a complementary limit face 40, not illustrated, of the locking groove 18 when the chuck 11 is in the retaining position. Overshooting the limit face 40 near the blade tip requires in this embodiment great forces, even with a leaf spring 14 biased only slightly inward.

Figure 18:
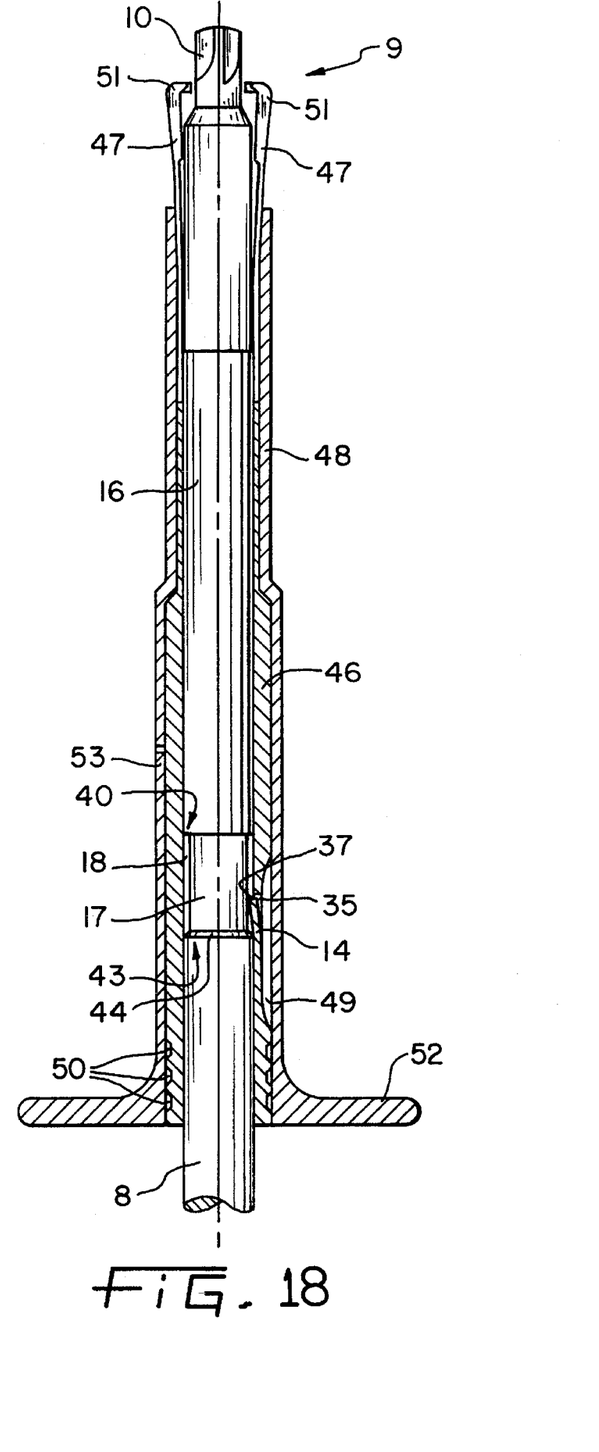
FIG. 18 is a partially cross sectional view of a further exemplary embodiment of a screwdriver according to the invention, with a driver blade according to FIG. 2 and a chuck fitted with outward-biased collets and a retaining sleeve slipped over it, partly in sectional view, in the area of the blade.

FIG. 18 shows, in a partially sectional view, the driver blade 8 according to FIG. 2 with a chuck 46 featuring collets 47 that are biased away from the driver blade 8, over a part of which a retaining sleeve 48 is slipped. The detent spring 14 is bent inward toward blade 8 and is an integral part of chuck 46 in an area of reduced material thickness comprising a relief 49 in the shell of the chuck 46. Also located on the chuck are gripping grooves 50, serving to facilitate removal of the chuck 46 from the retaining sleeve 48, for instance for cleaning. The gripping grooves 50 are recessed in the chuck 46 on its end nearest the grip part. Claws 51 are provided in the tip area 9 and, as shown in FIG. 18, leave an opening about the driver blade 8 on account of the outward bias of the collets 47. The material thickness of the collets 47 is greatest nearest claws 51.

For slipping the chuck 46 to its retaining position, the retaining sleeve 48 is fitted with a displacement dish 52 on the end of the retaining sleeve 48 nearest the grip part. Additionally, the retaining sleeve 48 possesses a second leaf spring, i.e., inhibitory spring 53. The inhibitory spring 53 is fabricated in a way similar to the detent spring 14 and is integral with the retaining sleeve 48. Inhibitory spring 53 is biased inward and bears on the outside of the chuck 46 with a contact force. The contact force displaces retaining sleeve 48 towards the blade tip 10 thereby safeguarding against an entrainment of the chuck 46 toward the blade tip 10 by creating an enhanced inhibitory force relative to the detent spring 14. The contact force produced by the inhibitory spring 53 is adjustable by using different widths and/or lengths of the detent spring 14 and inhibitory spring 53 and, after fabrication and frequent use, by bending the inhibitory spring in the appropriate amount and direction. By displacing the retaining sleeve 48 in the direction of the blade tip 10, the chuck 46 continues to be entrained until the stop face 37 of the detent spring 14 strikes the limit face 40 of the locking groove 18 nearest the blade tip.

Figure 19:
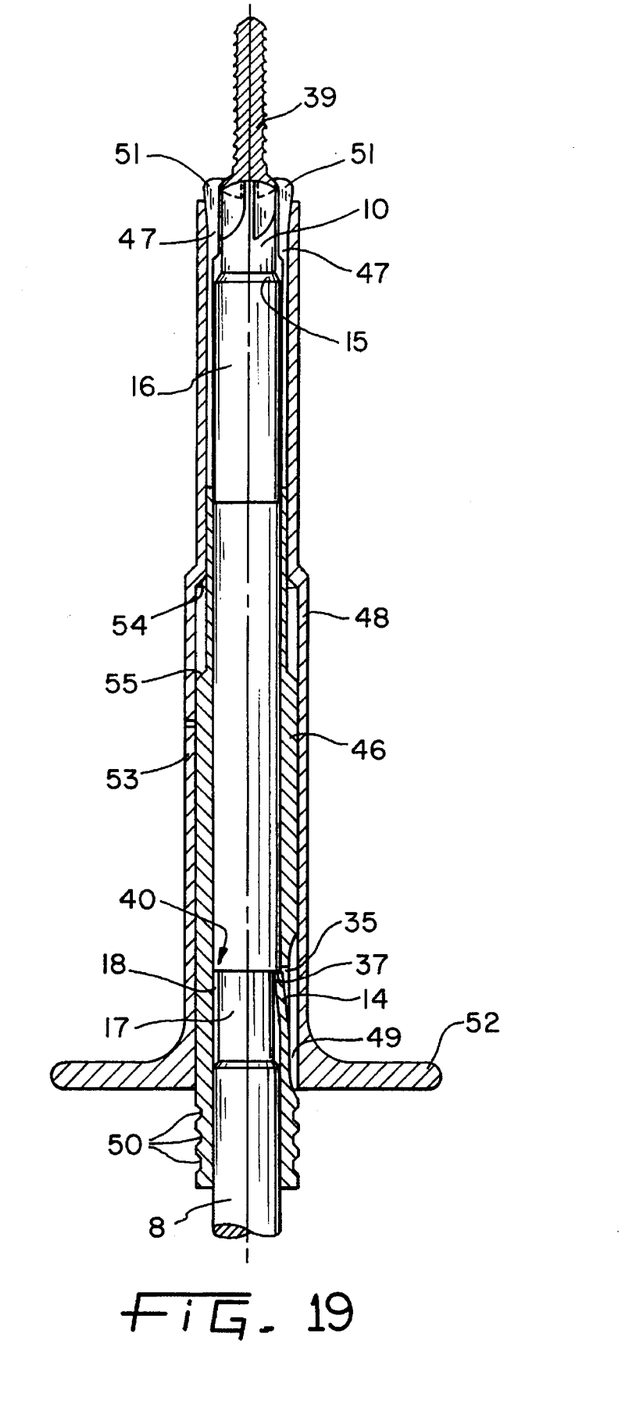
FIG. 19 is a partially cross sectional view of the arrangement according to FIG. 18 in the retaining position of the chuck and with the retaining sleeve in forward position, holding a screw.

FIG. 19 shows the screwdriver of FIG. 18 in the retaining position with a bone screw 39 being retained. The stop face 37 of the detent spring 14 engages the limit face 40 of the locking groove 18 nearest the blade tip, with the claws 51 gripping the head of the bone screw 39 and retaining sleeve 48 slipped onto and engaging the bulging area of the claws 51. The bone screw 39 is thus reliably retained by the retaining sleeve 48, despite the large lateral forces due to the enclosure of the claws 51.

To release the screw 39 being retained, the displacement dish 52 is retracted from the blade tip 10, removing retaining sleeve 48 from the claws 51 which then open outward due to their outward bias. The chuck 46 may be retracted towards grip part 2 so that a bevel 54 of the retaining sleeve 48 engages a bevel 55 on the chuck 46, thereby allowing claws 51 to spread.

While this invention has been described as having exemplary designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A screwdriver for bone screws comprising:

a grip;

a driver blade having a shank with a tip end and an opposing grip end, said tip end having a blade tip for engaging screws, said grip end being insertable into said grip;

a locking device preventing rotation and longitudinal movement of said driver blade relative to said grip; and a chuck enclosing said driver blade, said chuck being longitudinally displaceable relative to said driver blade;

a plurality of collets extending from an end of said chuck disposed adjacent to said blade tip, each of said collets being inwardly biased and having a claw disposed at an end of said collets opposite said chuck, whereby said claws retain a screw on said blade tip when said chuck is in a retaining position;

a blade tip bevel located on said driver blade and adapted to engage said claws thereby inhibiting the longitudinal displacement of said claws towards said grip end of said driver blade beyond said bevel; and a stop device comprising a stop face defining a portion of a groove surface, said groove located on said driver blade, and a detent spring located on said chuck, said detent spring having a free end extending towards said collets and biased inward, whereby said free end is disposed within said groove when said screwdriver is assembled and bears upon said stop face when said chuck is in said retaining position thereby inhibiting further longitudinal displacement of said chuck towards said blade tip.

2. The screwdriver of claim 1 wherein each of said collets further comprise a beveled step whereby said beveled steps engage said blade tip bevel as said chuck is displaced from said retaining position towards said grip end and thereby moving said claws outward into a screw disengaging position.

3. The screwdriver of claim 2 wherein said groove further comprises a recessed locking section surface, said locking section surface disposed between said stop face and said grip end, and wherein said stop face extends from an outer surface of said blade shaft to said recessed locking surface and is one of a stop shoulder substantially perpendicular to an axis of said blade shaft and a beveled surface forming an obtuse angle with said locking section surface.

4. The screwdriver of claim 2 wherein said stop face comprises a double step shoulder having a first and second shoulder surface substantially perpendicular to an axis of said blade shaft, and a substantially cylindrical surface separating said first and second shoulder surfaces, and wherein said detent spring further comprises a stepped surface adapted to engage said first and second shoulders.

5. The screwdriver of claim 2 wherein said groove further comprises a recessed locking section surface, said locking section surface disposed between said stop face and said grip end, and a limit face disposed between said recessed locking section surface and said grip end, said limit face comprising a beveled surface forming an obtuse angle with said locking section surface.

6. The screwdriver of claim 2 wherein said detent spring has one of a rectangular and a trapezoidal shape.

7. The screwdriver of claim 1 wherein said groove further comprises a recessed locking section surface, said locking section surface disposed between said stop face and said grip end, and wherein said stop face extends from an outer surface of said blade shaft to said recessed locking surface and is one of a stop shoulder substantially perpendicular to an axis of said blade shaft and a beveled surface forming an obtuse angle with said locking section surface.

8. The screwdriver of claim 7 wherein said groove further comprises a recessed locking section surface, said locking section surface disposed between said stop face and said grip end, and a limit face disposed between said recessed locking section surface and said grip end, said limit face comprising a beveled surface forming an obtuse angle with said locking section surface.

9. The screwdriver of claim 7 wherein said detent spring has one of a rectangular and a trapezoidal shape.

10. The screwdriver of claim 1 wherein said stop face comprises a double step shoulder having a first and second shoulder surface substantially perpendicular to an axis of said blade shaft, and a substantially cylindrical surface separating said first and second shoulder surfaces, and wherein said detent spring further comprises a stepped surface adapted to engage said first and second shoulders.

11. The screwdriver of claim 10 wherein said groove further comprises a recessed locking section surface, said locking section surface disposed between said stop face and said grip end, and a limit face disposed between said recessed locking section surface and said grip end, said limit face comprising a beveled surface forming an obtuse angle with said locking section surface.

12. The screwdriver of claim 10 wherein said detent spring has one of a rectangular and a trapezoidal shape.

13. The screwdriver of claim 1 wherein said groove further comprises a recessed locking section surface, said locking section surface disposed between said stop face and said grip end, and a limit face disposed between said recessed locking section surface and said grip end, said limit face comprising a beveled surface forming an obtuse angle with said locking section surface.

14. The screwdriver of claim 13 wherein said detent spring has one of a rectangular and a trapezoidal shape.

15. The screwdriver of claim 1 wherein said detent spring has one of a rectangular and a trapezoidal shape.

16. A screwdriver for bone screws comprising:

a grip;

a driver blade having a shank with a tip end and an opposing grip end, said tip end having a blade tip for engaging screws, said grip end being insertable into said grip;

a locking device preventing rotation and longitudinal movement of said driver blade relative to said grip; and a chuck enclosing said driver blade, said chuck being longitudinally displaceable relative to said driver blade;

a plurality of collets extending from an end of said chuck disposed adjacent to said blade tip, each of said collets being outwardly biased and having a claw disposed at an end of said collets opposite said chuck, said claws adapted to retain a screw on said blade tip when said claws are pressed inward;

a sleeve surrounding said chuck, said sleeve being longitudinally displaceable relative to said chuck, said sleeve engaging said collets and thereby pressing said claws inward when said chuck and sleeve are in a retaining position;

an inhibitory leaf spring located on said sleeve, said inhibitory spring biased inward and bearing on said chuck whereby frictional resistance to relative longitudinal displacement between said sleeve and said chuck is increased;

a blade tip bevel located on said driver blade forming a transition from a larger driver blade shank to a smaller blade shank portion terminating at said blade tip, said collets having a variable thickness which is greatest adjacent to said claws, whereby a thickest portion of said collets bears upon said smaller blade shank portion; and a stop device comprising a stop face defining a portion of a groove surface, said groove located on said driver blade, and a detent spring located on said chuck, said detent spring having a free end extending towards said collets and biased inward, whereby said free end is disposed within said groove when said screwdriver is assembled and bears upon said stop face when said chuck is in said retaining position thereby inhibiting further longitudinal displacement of said chuck towards said blade tip.

17. The screwdriver of claim 16 wherein said sleeve further comprises a first beveled stop adapted for engagement of a second beveled stop located on said chuck whereby said first beveled stop engages said second beveled stop when said sleeve is longitudinally displaced away from said claws.

18. The screwdriver of claim 17 wherein said groove further comprises a recessed locking section surface, said locking section surface disposed between said stop face and said grip end, and wherein said stop face extends from an outer surface of said blade shaft to said recessed locking surface and is one of a stop shoulder substantially perpendicular to an axis of said blade shaft and a beveled surface forming an obtuse angle with said locking section surface.

19. The screwdriver of claim 17 wherein said stop face comprises a double step shoulder having a first and second shoulder surface substantially perpendicular to an axis of said blade shaft, and a substantially cylindrical surface separating said first and second shoulder surfaces, and wherein said detent spring further comprises a stepped surface adapted to engage said first and second shoulders.

20. The screwdriver of claim 17 wherein said groove further comprises a recessed locking section surface, said locking section surface disposed between said stop face and said grip end, and a limit face disposed between said recessed locking section surface and said grip end, said limit face comprising a beveled surface forming an obtuse angle with said locking section surface.

21. The screwdriver of claim 17 wherein said detent spring has one of a rectangular and a trapezoidal shape.

22. The screwdriver of claim 16 wherein said groove further comprises a recessed locking section surface, said locking section surface disposed between said stop face and said grip end, and said stop face extends from an outer surface of said blade shaft to said recessed locking surface and is one of a stop shoulder substantially perpendicular to an axis of said blade shaft and a beveled surface forming an obtuse angle with said locking section surface.

23. The screwdriver of claim 22 wherein said groove further comprises a recessed locking section surface, said locking section surface disposed between said stop face and said grip end, and a limit face disposed between said recessed locking section surface and said grip end, said limit face comprising a beveled surface forming an obtuse angle with said locking section surface.

24. The screwdriver of claim 22 wherein said detent spring has one of a rectangular and a trapezoidal shape.

25. The screwdriver of claim 16 wherein said stop face comprises a double step shoulder having a first and second shoulder surface substantially perpendicular to an axis of said blade shaft, and a substantially cylindrical surface separating said first and second shoulder surfaces, and wherein said detent spring further comprises a stepped surface adapted to engage said first and second shoulders.

26. The screwdriver of claim 25 wherein said groove further comprises a recessed locking section surface, said locking section surface disposed between said stop face and said grip end, and a limit face disposed between said recessed locking section surface and said grip end, said limit face comprising a beveled surface forming an obtuse angle with said locking section surface.

27. The screwdriver of claim 25 wherein said detent spring has one of a rectangular and a trapezoidal shape.

28. The screwdriver of claim 16 wherein said groove further comprises a recessed locking section surface, said locking section surface disposed between said stop face and said grip end, and a limit face disposed between said recessed locking section surface and said grip end, said limit face comprising a beveled surface forming an obtuse angle with said locking section surface.

29. The screwdriver of claim 28 wherein said detent spring has one of a rectangular and a trapezoidal shape.

30. The screwdriver of claim 16 wherein said detent spring has one of a rectangular and a trapezoidal shape.

* * * * *